United States Patent
Roscher

(10) Patent No.: US 8,798,717 B2
(45) Date of Patent: Aug. 5, 2014

(54) PATIENT SUPPORT AND/OR TRANSPORT MEANS AND MAGNETIC RESONANCE SYSTEM

(75) Inventor: Bjarne Erik Roscher, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 519 days.

(21) Appl. No.: 12/825,413

(22) Filed: Jun. 29, 2010

(65) Prior Publication Data

US 2011/0004093 A1    Jan. 6, 2011

(30) Foreign Application Priority Data

Jul. 3, 2009 (DE) .......... 10 2009 033 065

(51) Int. Cl.
*A61B 5/055* (2006.01)
*A61G 13/10* (2006.01)
*A61G 1/02* (2006.01)

(52) U.S. Cl.
CPC ............ *A61B 5/0555* (2013.01); *A61G 1/0212* (2013.01); *A61G 1/0237* (2013.01); *A61G 1/0293* (2013.01); *A61G 2210/50* (2013.01)
USPC ........... 600/415; 600/424; 600/431; 382/131; 324/307; 5/601

(58) Field of Classification Search
CPC . A61B 5/0555; A61G 1/0212; A61G 1/0237; A61G 1/0293; A61G 2210/50
USPC .......... 600/407, 415, 424, 431; 382/128, 130, 382/131; 5/601; 324/307
See application file for complete search history.

(56) References Cited

U.S. PATENT DOCUMENTS

| | | | |
|---|---|---|---|
| 7,106,056 B2* | 9/2006 | Czipott et al. | 324/244 |
| 7,154,266 B2* | 12/2006 | Czipott et al. | 324/244 |
| 7,538,671 B2 | 5/2009 | Maschke | |
| 7,550,969 B2* | 6/2009 | Zhdanov | 324/243 |
| 7,570,064 B2* | 8/2009 | Roziere | 324/662 |
| 8,035,377 B2* | 10/2011 | Czipott et al. | 324/307 |
| 2004/0189293 A1 | 9/2004 | Czipott et al. | |
| 2006/0145691 A1* | 7/2006 | Massengill et al. | 324/207.25 |
| 2007/0132581 A1 | 6/2007 | Molyneaux et al. | |
| 2008/0097199 A1* | 4/2008 | Mullen | 600/431 |
| 2008/0242944 A1 | 10/2008 | Sharma | |
| 2008/0269596 A1* | 10/2008 | Revie et al. | 600/424 |
| 2010/0100348 A1* | 4/2010 | Artinger | 702/81 |
| 2010/0189328 A1* | 7/2010 | Boernert et al. | 382/131 |

FOREIGN PATENT DOCUMENTS

| | | |
|---|---|---|
| DE | 102004017185 A1 | 10/2005 |
| DE | 102005029787 A1 | 8/2006 |
| DE | 102008016770 A1 | 10/2008 |

* cited by examiner

*Primary Examiner* — Baisakhi Roy

(57) ABSTRACT

A patient support and/or transport device is proposed. The patient support and/or transport device comprises a receptacle in particular for a push-in patient support plate. At least one metal detection device is provided on the receptacle adjacent to the patient support plate when the patient support plate is pushed in.

16 Claims, 2 Drawing Sheets

US 8,798,717 B2

PATIENT SUPPORT AND/OR TRANSPORT MEANS AND MAGNETIC RESONANCE SYSTEM

CROSS REFERENCE TO RELATED APPLICATIONS

This application claims priority of German application No. 10 2009 033 065.8 filed Jul. 3, 2009, which is incorporated by reference herein in its entirety.

FIELD OF THE INVENTION

The invention relates to a means for supporting and/or transporting a patient, comprising a receptacle in particular for a push-in patient support plate, as well as to a magnetic resonance system.

BACKGROUND OF THE INVENTION

Many medical applications, in the field of imaging for example, but also for invasive interventions, need extremely strong magnetic fields which are frequently created by superconductive magnets. In addition to magnetic resonance imaging, field-based navigation systems for controlling invasive instruments introduced into the body could be cited as examples.

With these types of applications with high magnetic fields metal objects introduced unintentionally and/or without being discovered, especially ferromagnetic metal objects, represent a great risk. Moving metal objects represent an appreciable risk of injury.

There are thus known procedures for explaining these risks to patients in order to then request them to remove all metal objects. In addition the patient has to be asked about metallic implants. Furthermore it is also normal to examine patients or to scan them with a hand-held metal detector.

Such processes however require a patient who is able to respond or whose mental faculties are unimpaired. However it is occurring ever more frequently that the patient is subjected to such magnetic fields from time to time during the course of medical interventions. It is known for example that control images are recorded after or during an open intervention, for example an operation, in a magnetic resonance system. To this end the patient is generally placed on a patient support plate from which he must not be removed during the entire process. For this purpose the patient support plate can be moved by means of a patient transport means, typically a trolley, to different intervention and/or imaging locations where the patient support plate can then for example be pushed onto an operating table or onto the patient table of a magnetic resonance system. For example embodiments are known in which the patient support plate can be pushed from the patient transport means arranged on the foot side of the table in the longitudinal direction onto the patient table (i.e. a patient support means).

The patient is thus arranged permanently on the same patient support plate during the entire medical intervention and associated examinations and is mostly not able to respond. This increases the risk of metal objects on or in the patient or on the patient support plate being overlooked. In order to prevent this, working procedures are known so that for example the medical/surgical instruments employed are counted or the operation area is searched by hand and visually by the medical personnel. Despite this, especially with objects which are hidden, errors can occur in these cases and objects can be overlooked, which then present a risk of injury.

SUMMARY OF THE INVENTION

The underlying object of the invention is thus to specify a device which increases safety in connection with applications with a high magnetic field, especially when used within the framework of medical interventions in which the patient remains on a transportable patient support plate.

To achieve this object there is inventive provision with a patient support and/or transport means of the type mentioned at the start for at least one metal detection device to be provided on the receptacle adjacent to the patient support plate when the patient support plate is inserted.

The invention thus proposes integrating a metal detection device (frequently also abbreviated to metal detector) into a patient support and/or transport means so that the patient support plate, if it is inserted or pushed into the receptacle, is located at least partly in the detection range of the metal detection device. Ideally the entire surface of the inserted patient support plate is covered by the at least one metal detection device so that it can consequently be established whether metal/metal objects are to be found on the patient support plate or on the patient supported on the patient support plate. It should be stated even at this point however that embodiments are also conceivable in which the patient support plate can be examined while it is being pushed on to the patient support and/or transport means. If the patient support and/or transport means is embodied for example so that the patient support plate is pushed into the receptacle from the foot side in the longitudinal direction, the at least one metal detection device can be provided on the foot side so that all areas of the patient support plate are moved through the detection area of the metal detection device as it is being pushed in.

Metal detection devices are widely known and do not need to be explained in greater detail. They generally comprise a search coil to which a high-frequency alternating current or an impulse is imparted. If an electrically-conductive material is located in the vicinity of the search coil, energy currents are induced in the metal so that a separate modified magnetic field arises. This can then be measured, for example with a further coil, which functions as a magnetometer.

Other variants are naturally also conceivable, so that in the present invention any type of metal detection device can be employed.

An integral solution is thus created with the present invention in order to be able to automatically locate metallic objects on the patient support plate or on/in the patient respectively. This is especially advantageous for people who are not mentally aware since they cannot themselves assist in finding metallic objects. The safety of the clinical workflow is enhanced since this type of checking by a metal detection device is less susceptible to errors and in any event a check is undertaken before the patient with the patient support plate is moved into the high magnetic field, especially into the magnetic resonance system.

For medical, especially surgical interventions, with magnetic resonance support in particular, in which a patient is regularly moved into the patient support of a magnetic resonance system in order to check the progress of the treatment, safety is increased since the medical personnel are given a further means for checking overlooked medical devices on the patient.

Especially advantageously there can be provision in an area adjacent to the inventive patient support plate for a number of metal detection devices to be arranged, which at least partly cover the surface of the inserted patient support plate, especially in the form of a matrix. In this exemplary embodiment ultimately different sectors of the patient support plate are defined to which a metal detection device is assigned. In this case, in an especially advantageous embodiment, the entire surface of the patient support plate can be covered in the form of a matrix by a corresponding number of metal detection devices. This means that in an advantageous manner, as well as the information as to where the metal is present, location information can also be obtained by the sector or the sectors being determined in which the metal detection device has responded. There can also especially be provision for the patient support plate to be divided up symmetrically into different sectors so that a matrix of rectangular surfaces is produced. Integrated into the patient support and/or transport means adjacent to these rectangular surfaces is a metal detection device in each case, the detection area of which corresponds to the relevant sector. When a number of metal detection devices are used there can generally be provision for the metal detection devices to be able to be controlled and/or read out individually and/or in groups. This makes it possible to read out the approximate position of the metallic object on the patient support plate. The accuracy increases or reduces depending on the size of the said sectors.

It should be stated at this point that location information can also be obtained if the measurement is undertaken by scanning the patient support plate with one or with a few metal detection devices while the patient support plate is moving past the metal detection device or devices. Then not only information that metal has been detected can be recorded but also the point in time which can be related to a coordinate or an area in the direction of movement of the patient support plate. For example an analysis device can be provided which is embodied for carrying out these steps.

Expediently there can be provision for the metal detection device or the metal detection devices to include a transceiver unit, especially embodied for wireless communication. The transceiver unit is on the one hand embodied for receiving control signals for the metal detection device, especially activation or deactivation signals respectively. The measured sensor data can also be passed on to an analysis device which can also be realized at least partly in the metal detection device, which will be discussed in greater detail below. Although it is entirely conceivable to transport the sensor data over a cable it is however more advantageous for provision to be made for the transceiver unit to be embodied for wireless communication, especially for radio and/or infrared communication with an analysis device. No expensive cabling is then needed and there can especially be provision for the at least one metal detection device to be able to be activated or read out via an external analysis device or control device. Especially with an embodiment as a patient support means, especially as a patient table, the activation and the readout of the at least one metal detection device can then be possible via a magnetic resonance system or the like.

As already mentioned, the patient support and/or transport means can include an analysis device for processing the sensor data of the metal detection device. The analysis device, which can consist of a number of analysis units, some of which can especially be provided in the metal detection device, ultimately determines whether metal has been detected. If a number of metal detection devices are provided the analysis device can also be embodied to determine the approximate position, for example the sector, in which the metal was identified. Also conceivable here, if the number of metal detection devices respond, is an interpolation for more precise determination of the location. A very wide variety of embodiments are conceivable here.

In order to provide an operator, especially the medical personnel, with the information that metal is present, the patient support and/or transport means can further be provided with an output means for outputting a warning when metal is detected. In such cases this can typically involve an optical output means, especially a screen and/or a warning light, and/or an acoustic output means, especially a loudspeaker. Thus for example warning tones can be emitted if metal has been detected on the patient support plate. If the screen is used, it is especially also possible, when a number of metal detection devices are used, to display the location, for example in a graphical representation, at which the metal is located, especially by highlighting a sector of the patient support plate, as has already been discussed in greater detail above.

In an especially advantageous embodiment of the present invention there can be provision for the patient support and/or transport means to include a blocking device for locking an inserted patient support plate in place if metal is detected. In this way a safety interlock is created which initially prevents the introduction of the patient support plate into the area of the high magnetic field, especially the patient support of a magnetic resonance device. Such a blocking device can be electrical and/or mechanical for example, meaning that a resistance can be created or even, by means of a lock for example, the plate can be locked in place completely. Consequently a mechanical/electrical hurdle is created on the introduction of the patient into the high magnetic field which can only be overcome actively and explicitly by the medical personnel. To this end, in a further expedient embodiment, there can be provision for a control element, especially a switch, to be provided for triggering the blocking device. Such a control element can for example be used if the metallic object has been found and removed and/or has been found to be non-critical. Naturally an embodiment is also conceivable in which the blocking device, for example activated by the analysis device, is then released again if the metal detection device does not discover any further metal on the patient support plate. The safety interlock then remains active for exactly as long as metal has actually been detected. Naturally the control element and the automatic release of the block when no further metal is present can be combined as an embodiment.

The patient support and/or transport means can typically be a transport wagon for a patient support plate, for example a trolley. Such transport means are used to transport the patient support plate, from which the patient may not be removed during a medical intervention, from one deployment location, for example an operating table, to another, for example a patient table of a magnetic resonance system. If necessary a check can then be made here at any time, for example en route to a magnetic resonance system, as to whether there is still metal present on the patient support table. However there can also be provision for the patient support means to be a patient table of a magnetic resonance system or of a magnetoencephalography device. An integrated solution is then created at the location where problems can occur with too high magnetic fields or a measurement falsification as a result of metals in order to examine patient support plates with the patients supported on them for metallic objects and thus increase the safety.

As well as the patient support and/or transport means, the invention also relates to a magnetic resonance system comprising a patient support and/or transport means in accordance with one of the previous claims. In this way the patient support and/or transport means is assigned directly to the magnetic resonance system and can especially advantageously be integrated into the overall structure or into the overall operation of the magnetic resonance system.

Thus the magnetic resonance system can typically comprise a control device embodied for communication with a transceiver unit of the metal detection device and for activating and also for reading out the metal detection device. The control device which here again can also include the analysis device completely or in part is not provided in this case on the patient support and/or transport means, but is part of the magnetic resonance system, which is especially advantageous with a transceiver unit embodied for wireless communication.

In an expedient further embodiment the magnetic resonance system can comprise an output means for outputting a warning if metal is detected. The output means, which is controlled accordingly by the control device, can replace an output means arranged on the patient support and/or transport means, however there can also be provision for an output means to be arranged both on the patient support and/or transport means and also on the magnetic resonance system, for example on an operating console of the magnetic resonance system. The output means can be embodied in this case as an optical output means, especially a screen and/or a warning light, and/or as an acoustic output means, especially a loudspeaker. Especially advantageously output means present in any event on the magnetic resonance system, for example an operating console, can also be used.

If the patient support and/or transport means comprises a blocking device for locking the inserted patient support plate in place if metal is detected, the magnetic resonance system can include a control element, especially a switch for triggering a blocking device provided on the patient support and/or transport means. The control element can consequently likewise be provided on an operating console of the magnetic resonance system so that a warning/an alert can be output there centrally and/or the blocking device can be switched.

BRIEF DESCRIPTION OF THE DRAWINGS

Further advantages and details of the present invention emerge from the exemplary embodiments presented below as well as with reference to the drawings. The figures show.

DETAILED DESCRIPTION OF THE INVENTION

Figure 1:
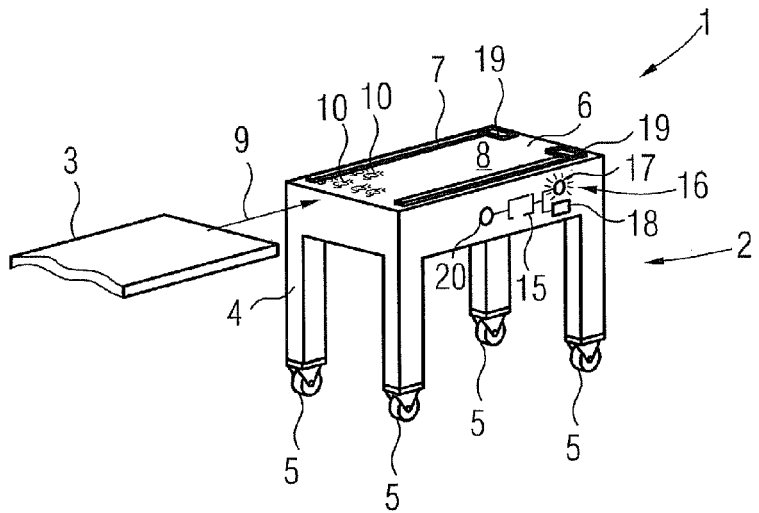
FIG. 1 an inventive patient support and transport means.

FIG. 1 shows an inventive patient support and transport means 1. This involves a transport wagon 2 for a patient support plate labeled 3, which can be pushed onto the transport wagon 2 in the longitudinal direction in order for example to move the patient from an operating table to a control imaging facility at a magnetic resonance system.

The transport wagon 2 comprises a chassis 4 on which four castors 5 are arranged, to simplify movement of the transport wagon. An upper surface 6 with a rail system 7 forms a receptacle 8 for the patient support plate 3 which can be pushed on in the direction of the arrow 9, i.e. in a longitudinal direction. Other variants are naturally also conceivable for embodying the receptacle 8 for the patient support plate 3. For example a form-fit receptacle in a recess or the like can be provided.

Figure 2:
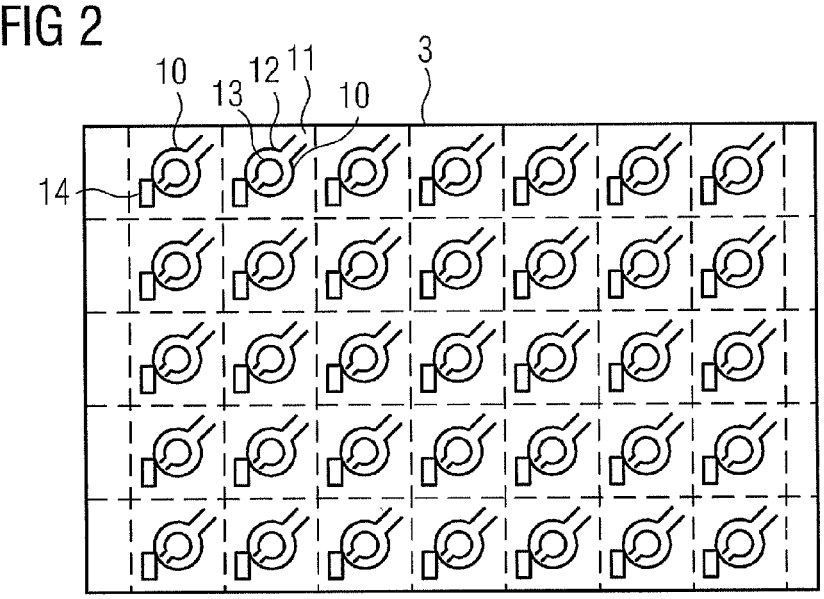
FIG. 2 an overhead view of the inventive patient support and transport means, FIG. 3 an inventive magnetic resonance system, and FIG. 4 a possible display on an inventive magnetic resonance system.

Let into the surface 6 are now a number of metal detection devices 10, only partly indicated in FIG. 1, which are arranged so that they are adjacent to the patient support plate 3 pushed into the receptacle 8 and cover its surface in the form of the matrix, which is shown in greater detail by FIG. 2.

FIG. 2 shows an overhead view of the inserted patient support plate 3. Below the patient support plate 3 and adjacent to the plate are now located the metal detection devices 10 which are arranged let into the surface 6 in the form of a matrix. It can be seen that the detection area of each of the metal detection devices 10 essentially covers a rectangular area 11 of the patient support plate 3, as indicated in FIG. 2 by the dashed lines. Use of such metal detection devices 10 covering the patient support plate 3 (and a patient supported thereon) in the form of a matrix also enables location information about detected metal to be obtained.

In the present exemplary embodiment metal detection devices 10 are used which comprise a search coil 12 creating an alternating field or a current pulse and a receive coil 13. Furthermore a transceiver unit 14 is also be provided for each metal detection device 10, which can also include parts of an analysis device. Control signals are received wirelessly, for example via radio or infrared by the transceiver unit, for example the activation or deactivation of the metal detection device 10 and measured sensor data is communicated to the analysis device 15 which is shown indicated in FIG. 1. In the analysis device 15, which can also serve as a control device for the entire metal detection system of the patient support and transport means 1, the sensor data of the metal detection device 10 is processed and the information as to whether metal is located on the patient support plate 3 or on a patient supported thereon, as well as if necessary information about the approximate position of the metal, is deduced.

It should be noted at this point that such position information can also be obtained when fewer, especially only one, metal detection device 10 is used and is arranged so that the patient support plate 3 is covered when pushed in or pulled out. Thus there can be provision for example for one or a number of metal detection devices 10 to be arranged only in the foot-side and/or head-side area of the surface 6, from where the patient support plate 3 is pushed in, whereby as well as the information that metal has been detected, the time of detection is also recorded and used to obtain location information at least in the longitudinal direction.

Two output means 16 are further provided on the transport wagon, namely a warning light 17 and a loudspeaker 18. If metal is detected the warning light, for example an LED, illuminates and an acoustic warning signal is given so that medical personnel are alerted to the fact that there is still metal on the patient support plate 3 and/or in/on a patient supported thereon. It is additionally also conceivable to provide an output means on the transport wagon 2 itself which indicates the position at which metal has been detected. For example an abstracted representation of the patient support plate 3, for example in the form of the rectangles 11, can be provided, with each of the rectangles shown in this representation being assigned a warning light, which then also lights if metal has been detected in the corresponding real rectangular detection area. Screens or the like are also conceivable.

It should however be noted at this point that the sensor data or the analysis results can also be transferred to an external device, typically the control device of a magnetic resonance system either by the analysis device 15 or by the metal detection devices 10 themselves, where the information can then be displayed for example on a console of a magnetic resonance system, especially on a screen there.

When metal is detected a second measure is provided in the exemplary embodiment depicted in FIG. 1 for which a mechanical blocking device 19 is used. If metal is detected, the patient support plate 3 can thus be locked in place by the blocking device 19, so that it can no longer be removed from the receptacle 8. This avoids the patient support plate 3 being moved into a higher magnetic field when dangerous metal objects may still be present on it.

Furthermore a control element 20 is provided via which the locking can be released again by the blocking device 19. The control element 20 can also have a multiple function here: For example it can also be used to only initiate a check of the patient support plate 3 for metal, i.e. activate the metal detection devices 10, to enable any metal that may be present on the patient support plate 3 to be sensed and to analyze the corresponding sensor data. If metal has been found, this can be removed and the locking device 19 can be released again by the control element 20, in this case a knob. If necessary a further check can also be undertaken on actuation of the control element 24 for releasing the blocking device 19, i.e. sensor data can be recorded from the metal detection devices 10 again to check for the metal has actually been removed.

As has already been explained, the patient transport and support means 1 presented can also be explicitly assigned to a magnetic resonance system and thereby form a part of the latter.

Figure 3:
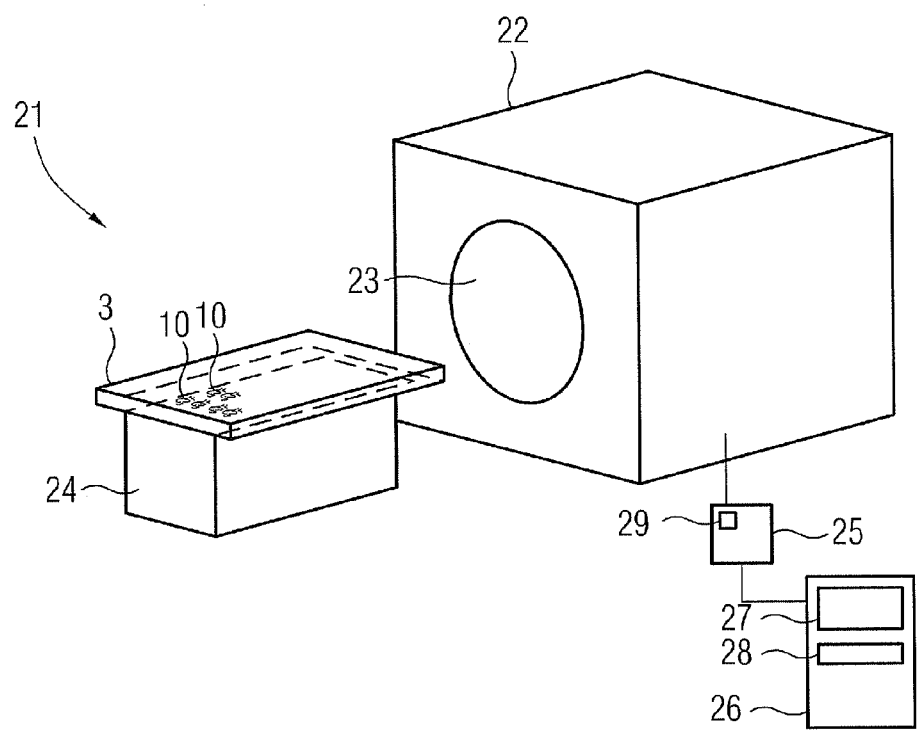

FIG. 3 now shows an inventive magnetic resonance system 21. In a manner which is already known and will thus not be presented in any more detail here, it includes a magnet unit 22 with a basic field magnet, the gradient coils, the high-frequency coils etc. The magnet unit 22 features a patient chamber 23 into which the patient support plate 3 can be moved from a patient table 24. During operation, for example if magnetic resonance images are to be recorded during an operation for checking purposes, the patient support plate 3 can be moved any number of times from its receptacle not described in any greater detail here on the patient table 24 into the patient chamber 23 and back again. It is also conceivable, if the medical intervention is taking place at another location, for the patient to be initially moved onto the patient support plate 3 with a transport wagon/trolley, the patient support plate 3 to then be pushed onto the patient table 24, from where the patient support plate 3 controlled by a control device 25 of the magnetic resonance system can be moved to be received into the patient chamber 23. An operating console 26 of the magnetic resonance system 21 with an optical means of output, in this case a screen 27 and an input device 28 are further provided, via which the magnetic resonance system 21 is controlled.

Also integrated into the patient table 24, precisely as in the exemplary embodiment in accordance with FIGS. 1 and 2, are schematically-indicated metal detection devices 10 which cover the patient support plate 3, as depicted in FIG. 2, in the form of a matrix in their detection areas. The information relating to these devices can also be transferred analogously to the present example which relates to the patient table of a magnetic resonance system 21.

By contrast with the exemplary embodiment discussed in relation to FIGS. 1 and 2, the transceiver units 14 embodied for wireless communication do not communicate here with an analysis device provided in the patient table 24 but instead the analysis device 29 forms a part of the control device 25 of the magnetic resonance system 21. There the wirelessly-transmitted sensor data, as already described in relation to the patient support and transport means 1, is analyzed in respect of the presence of metal and of its position, after which a display can be presented on the screen 27. It should be pointed out that here too of course further output means, especially also provided on the patient table 24, can be added in order to further alert the medical personnel to the metal object which has been detected.

Figure 4:
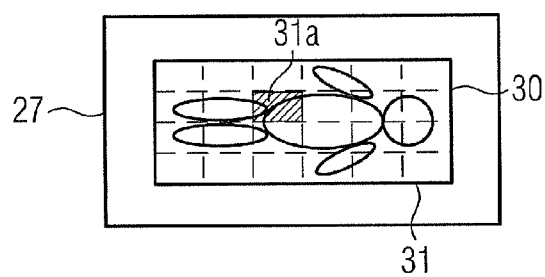

A possible display on the screen 27 is shown in FIG. 4. It comprises a schematic diagram 30 of the patient support plate 3 with the various detection areas 31. A detection area 31a is shown clearly highlighted in red. This indicates that a metal object has been detected by the metal detection device 10 assigned to this detection area 31a, so that this object can be searched for explicitly.

In the present example the control device 25 is also embodied to at least initially block any movement of the patient support plate 3 into the patient chamber 23 if a signal indicating metal has been determined by the metal detection devices 10. In this way it is ensured that no dangerous metal is introduced with a patient into the patient chamber 23. This blocking can be cancelled again by the medical personnel at the operating console 26, with if necessary a further check being undertaken for safety's sake by the metal detection devices 10.

The invention claimed is:

1. A device for supporting and/or transporting a patient, comprising:
    a patient support plate;
    a receptacle for inserting the patient support plate;
    a metal detection device arranged on an upper surface of the receptacle and below the inserted patient support plate for detecting a metal object on the inserted patient support plate;
    a blocking device for locking the inserted patient support plate in place if the metal object is detected on the inserted patient support plate; and
    a control element for releasing the blocking device if the metal object is removed and no further metal object is detected on the patient support plate.

2. The device as claimed in claim 1, further comprising a plurality of metal detection devices which at least partly cover a surface of the inserted patient support plate.

3. The device as claimed in claim 2, wherein the metal detection devices are arranged as a matrix.

4. The device as claimed in claim 2, wherein the metal detection devices are able to be activated and/or read out individually and/or in groups.

5. The device as claimed in claim 1, wherein the metal detection device comprises a transceiver unit for wireless communication.

6. The device as claimed in claim 1, further comprising an analysis unit for processing a sensor data of the metal detection device.

7. The device as claimed in claim 1, further comprising an output device for outputting a warning when the metal object is detected.

8. The device as claimed in claim 7, wherein the output device comprises an optical output device comprising a screen and/or a warning light.

9. The device as claimed in claim 7, wherein the output device comprises an acoustic output device comprising a loudspeaker.

10. The device as claimed in claim 1, wherein the blocking device is an electrical or a mechanical device.

11. The device as claimed in claim 1, wherein the device comprises a transport wagon, a patient table of a magnetic resonance system, or a magnetoencephalography device.

12. A magnetic resonance system, comprising:
a patient table according to claim 1; and
a magnet unit comprising a patient chamber into which the inserted patient support plate can be moved from the patient table.

13. The magnetic resonance system as claimed in claim 12, further comprising a control device for communicating with a transceiver unit of the metal detection device and for activating as well as reading out sensor data of the metal detection device.

14. The magnetic resonance system as claimed in claim 12, further comprising an output device for outputting a warning when the metal object is detected.

15. The magnetic resonance system as claimed in claim 14, wherein the output device comprises an optical output device comprising a screen and/or a warning light.

16. The magnetic resonance system as claimed in claim 14, wherein the output device comprises an acoustic output device comprising a loudspeaker.

* * * * *